(12) United States Patent
Zhu et al.

(10) Patent No.: US 11,059,843 B2
(45) Date of Patent: Jul. 13, 2021

(54) STEVIOSIDE M CRYSTAL FORM, PREPARATION METHOD THEREFOR AND USE THEREOF

(71) Applicant: ZHUCHENG HAOTIAN PHARM CO., LTD., Shandong (CN)

(72) Inventors: Liping Zhu, Shandong (CN); Xuefeng Mei, Shandong (CN); Ying Huang, Shandong (CN); Jianrong Wang, Shandong (CN)

(73) Assignee: ZHUCHENG HAOTIAN PHARM CO., LTD., Shandong (CN)

( * ) Notice: Subject to any disclaimer, the term of this patent is extended or adjusted under 35 U.S.C. 154(b) by 0 days.

(21) Appl. No.: 16/494,681

(22) PCT Filed: Mar. 14, 2018

(86) PCT No.: PCT/CN2018/079010
§ 371 (c)(1),
(2) Date: Sep. 16, 2019

(87) PCT Pub. No.: WO2018/166475
PCT Pub. Date: Sep. 20, 2018

(65) Prior Publication Data
US 2020/0010497 A1    Jan. 9, 2020

(30) Foreign Application Priority Data

Mar. 16, 2017 (CN) .......................... 201710157466.6

(51) Int. Cl.
*C07H 15/24* (2006.01)
(52) U.S. Cl.
CPC .......... *C07H 15/24* (2013.01); *C07B 2200/13* (2013.01)

(58) Field of Classification Search
None
See application file for complete search history.

(56) References Cited

U.S. PATENT DOCUMENTS

2015/0344512 A1* 12/2015 Prakash ................ B01D 15/08
536/18.1

FOREIGN PATENT DOCUMENTS

| CN | 103397064 A | 11/2013 | |
|---|---|---|---|
| CN | 103739639 A | 4/2014 | |
| CN | 103739640 A | 4/2014 | |
| CN | 103757074 A | 4/2014 | |
| CN | 104151378 A | 11/2014 | |
| CN | 104163839 A | 11/2014 | |
| CN | 104726523 A | 6/2015 | |
| CN | 105037458 A | 11/2015 | |
| CN | 105722533 A | 6/2016 | |
| WO | WO-2016130609 A1 * | 8/2016 | ............. A23L 27/36 |

* cited by examiner

*Primary Examiner* — Traviss C McIntosh, III
(74) *Attorney, Agent, or Firm* — Novick, Kim & Lee, PLLC; Bin Lu; Zhi Yang Xue

(57) ABSTRACT

The present invention relates to a stevioside M crystal form, a preparation method therefor and a use thereof, and specifically, relates to a naturally extracted high-intensity sweetener, i.e., a stevioside M crystal form A, the preparation method therefor and the user thereof. By means of comprehensive characterization of the new crystal form, the new crystal form is found to have advantages such as a high degree of crystallinity, good stability, and low hygroscopicity, and is applicable to a more comprehensive field of application. The preparation method in the present invention is simple and easy to operate, has high selectivity and good reproducibility, and can stably obtain the target crystal form.

7 Claims, 6 Drawing Sheets

STEVIOSIDE M CRYSTAL FORM, PREPARATION METHOD THEREFOR AND USE THEREOF

TECHNICAL FIELD

The present invention relates to the field of sweeteners, in particular to a novel crystal form of stevioside M, a preparation method therefor and a use thereof.

BACKGROUND

*Stevia rebaudiana* is native to the Amanbai Mountains bordering Brazil and Paraguay in South America. It is a plant with high sweetness. The white powdered stevioside extracted from *Stevia rebaudiana* is a natural, high sweetness, zero-calorie sweetener and natural sugar substitute. Stevioside is the third-best-selling product in the international high-intensity sweetener market. The first-generation stevioside is mainly mixed sugars, but it is often accompanied by a bitter taste. The second generation of stevioside is mainly high-purity stevioside A, and has been widely used in foods, health care products and medicines. With the increasing popularity of stevioside A, other glycosides in *Stevia rebaudiana* have also gradually received attention. Currently, in addition to stevioside A, stevioside compounds which are used on the market further include stevioside B, stevioside C, stevioside D and stevioside M. Among them, stevioside D and stevioside M have the best taste, and have no post-bitter taste of stevioside A, and have been approved by the FDA as a novel sweetener.

Stevioside M (also known as Rebaudioside M or Rebaudioside X, Reb M), (13-[(2-O-β-D-pyranoglucosyl-3-O-β-D-pyranoglucosyl-β-D-pyranoglucosyl)oxyl]-ent-kauran-16-en-19-oic acid-[(2-O-β-D-pyranoglucosyl-3-O-β-D-pyranoglucosyl-β-D-pyranoglucosyl) ester] is isolated from *Stevia rebaudiana*.

Stevioside M is present in *Stevia rebaudiana* in trace amounts (0.05% to 0.5% by weight). Patent CN 104151378 A discloses a method of purifying stevioside M. However, due to the low content of natural stevioside M, most studies on stevioside M have turned to enzyme conversion or synthesis processes. Patent CN 104726523 A discloses a method for producing stevioside M using stevioside A and sucrose as raw materials with the use of the tomato UDP-glycosyltransferase and the potato sucrose synthase. Patent CN 104163839 A discloses a method in which a stevioside C is used as a substrate and a substitution reaction with a compound R1 under the action of silver carbonate is performed to obtain an intermediate Ac-Reb M, followed by hydrolysis to obtain a stevioside M product. Patent CN 103397064 A discloses a method of producing stevioside M, wherein, using stevioside A or stevioside D as a substrate in the presence of a glucosyl donor, under the catalysis of UDP-glucosyltransferase and/or recombinant cells containing UDP-glucosyltransferase, the substrate reacts to form a stevioside M. The above method has the disadvantages of high production cost, harsh reaction conditions, and difficulty in preparing high-purity stevioside M.

Crystal Stevioside M has poor water solubility and solubility qualities in beverage formulations. The stevioside M having a content of 75% to 90% has a solubility of from 0.1% to 0.15% in water at room temperature. Patent CN 105722533 A reports the improvement of stevioside M solubility by a combination of stevioside D and at least one surfactant. Among them, an amorphous composition of stevioside M and stevioside D can increase the solubility of stevioside M to 0.3% (w/w). Although the water solubility of the stevioside M is slightly increased, the stability of the composition is unpleasant due to its amorphous nature.

It is well known that different crystal forms may cause differences in color, morphology, stability, hygroscopicity and solubility, which in turn affect the storage conditions, appearance and taste of the food. The different crystal form of the stevioside compound has a great influence on its taste, stability, hygroscopicity and solubility. Patents CN 103739639 A and CN 103739640 A report two crystal forms of stevioside A, wherein the crystal form 7 has the advantages of good taste and low hygroscopicity, and the crystal form 9 has the advantages of high stability and high water solubility. The crystal form A of stevioside D disclosed in the patent CN 105037458 A has the advantages of high crystallinity, good water solubility and high chemical stability. At present, studies on the crystal forms of stevioside A, stevioside B, stevioside C and stevioside D have been reported, and the crystal form of stevioside M with the best taste has never been reported.

There is an urgent need in the art to provide a crystal form of stevioside M having better performance, such as a new crystal form having good crystallinity, good water solubility, high chemical stability and good taste. At the same time, there is an urgent need to provide a preparation method and a use for the above crystal forms.

SUMMARY OF THE INVENTION

The present invention intends to provide a novel crystal form of stevioside M.

Another object of the present invention is to provide a method for the preparation of the novel crystal form of stevioside M.

A further object of the present invention is to provide a use of the novel crystal form of stevioside M.

In a first aspect of the present invention, it provides a crystal form A of stevioside M, in an X-ray powder diffraction method using Cu-Kα, the crystal form A has distinct characteristic diffraction peaks at about 4.30, 6.57, 8.04, 16.31, 17.57 and 20.91, with the 2θ angles expressed in degrees.

In another preferred embodiment, the crystal form A has an X-ray powder diffraction (XRPD) pattern as shown in FIG. 1, and a 2θ value expressed in degrees with an error range of ±1°, and an interplanar spacing d expressed in Å and a relative intensity of the diffraction peaks expressed in percentage having the following characteristics:

| 2θ angle | d | relative intensity % |
|---|---|---|
| 3.51 | 25.12 | 14.4 |
| 4.30 | 20.54 | 63.7 |
| 5.27 | 16.75 | 17.7 |
| 6.57 | 13.44 | 54.4 |
| 8.04 | 10.99 | 100.0 |
| 13.43 | 6.59 | 28.8 |
| 14.61 | 6.06 | 39.9 |
| 16.31 | 5.43 | 59.5 |
| 17.57 | 5.04 | 87.7 |
| 18.34 | 4.83 | 40.8 |
| 19.25 | 4.61 | 22.5 |
| 19.75 | 4.49 | 32.1 |
| 20.91 | 4.24 | 42.6 |
| 22.56 | 3.94 | 31.5 |
| 23.67 | 3.76 | 19.5 |
| 3.51 | 25.12 | 14.4 |
| 4.30 | 20.54 | 63.7 |
| 5.27 | 16.75 | 17.7 |

-continued

| 2θ angle | d | relative intensity % |
|---|---|---|
| 6.57 | 13.44 | 54.4 |
| 8.04 | 10.99 | 100.0 |
| 13.43 | 6.59 | 28.8 |

In another preferred embodiment, the crystal form A has a differential scanning calorimetry pattern as shown in FIG. 2, and has characteristic endothermic peaks in the interval of about 30-160° C. and 210-250° C.

In another preferred embodiment, the thermogravimetric analysis of the crystal form A begins to decompose at 250±20° C.

In another preferred embodiment, the crystal form A has a dynamic moisture adsorption profile as shown in FIG. 4. The mass percentage of moisture absorption is 0-9.4% within a relative humidity of 0-40%, and the mass percentage of moisture absorption is 9.4-14.0% within a relative humidity of 40-80%.

In another preferred embodiment, the crystal form A has characteristic peaks at least at 3391 $cm^{-1}$, 2922 $cm^{-1}$, 1727 $cm^{-1}$, 1639 $cm^{-1}$, 1446 $cm^{-1}$, 1365 $cm^{-1}$, 1228 $cm^{-1}$, 1202 $cm^{-1}$, 1074 $cm^{-1}$, 1032 $cm^{-1}$, 991 $cm^{-1}$, 891 $cm^{-1}$, 637 $cm^{-1}$ and 560 $cm^{-1}$ in an infrared spectrum with an error range of ±2 $cm^{-1}$.

In a second aspect of the present invention, it provides a method for producing a crystal form A of Stevioside M as described above, which is a mixed crystallization method of one or two or more of a suspension method, a solution evaporation method or a cooling method, comprising the following steps:

(1) suspending: mixing stevioside M with a solvent for 0.1-48 h in a temperature range of 0-100° C. to obtain a suspension solution;

(2) cooling: filtering the suspension solution in step (1) while hot, and cooling the filtrate to a temperature range of 0-30° C. until a large amount of white solid is precipitated to obtain a suspension solution;

(3) volatilization: under a vacuum pressure less than or equal to 0.1 MPa, volatilizing the suspension solution in step (1) in a temperature range of 0-100° C. after filtering until a large amount of white solid is precipitated to obtain a suspension solution; and (4) filtration: filtering or centrifuging the suspension solution in step (1), (2) or (3) in a temperature range of 0-100° C. to obtain a white solid, which is dried to obtain a crystal form A of stevioside M.

In another preferred embodiment, the dry matter purity of the stevioside M in step (1) is in a range of 20-100%.

In another preferred embodiment, the solvent in step (1) is: one or two or more of methanol, ethanol, 1-propanol, acetonitrile, acetone, methyl ethyl ketone, methyl acetate, ethyl formate, ethyl acetate, methyl ter-butyl ether, tetrahydrofuran, nitromethane and methylbenzene, or a mixed solvent of the above solvent and water.

In a third aspect of the present invention, it provides a use of the crystal form A of stevioside M provided by the present invention as described above for the preparation of foods, health care products and medicines.

In another preferred embodiment, it provides a use of the crystal form A of stevioside M provided by the present invention as described above in a composition.

In another preferred embodiment, the composition is selected from the group consisting of: a food composition, a beverage composition, a health care product composition, and a pharmaceutical composition.

The preparation method of the crystal form A of stevioside M provided by the invention has the advantages of simple process and easy operation, and the obtained product has high crystallinity, low hygroscopicity and high stability.

It should be understood that, within the scope of the present invention, each technical feature of the present invention described above and in the following (as examples) may be combined with each other to form a new or preferred technical solution, which is not listed here due to space limitations.

DETAILED DESCRIPTION

Figure 1:
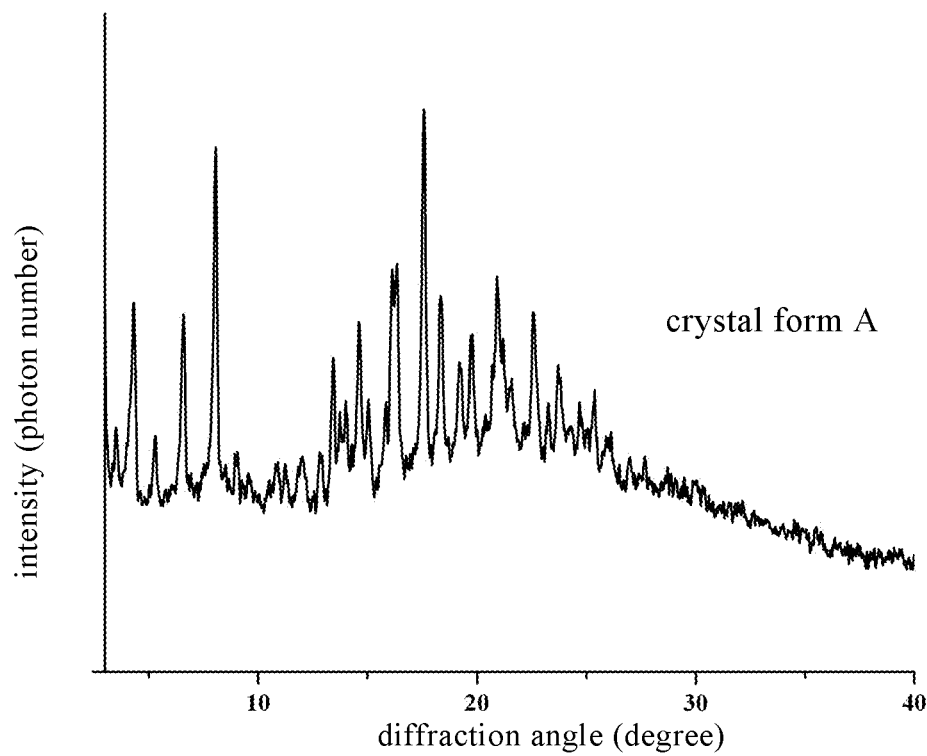
FIG. 1 is an X-ray powder diffraction (XRPD) pattern of the crystal form A of stevioside M provided by the present invention.

After an extensive and in-depth study, the present inventors have for the first time developed a crystal form A of stevioside M, and the crystal form A has high crystallinity, good chemical stability and low hygroscopicity, and its preparation process is simple, efficient and of a good repeatability, and it can realize large-scale industrial production. On this basis, the inventors complete the present invention.

Terms

All technical and scientific terms used herein have the same meaning as commonly understood by the skilled in the art to which this invention belongs, unless otherwise defined.

As used herein, when used in reference to a particular recited value, the term "about" means that the value can vary by no more than 1% from the recited value. For example, as used herein, the expression "about 100" includes 99, 100 and all values between 99 and 101 (such as, 99.1, 99.2, 99.3, 99.4, etc.).

For a characteristic diffraction peak represented by a 2 theta angle, the term "about" means that the recited value varies by no more than 2°, for example about X°, which means X±2°, preferably X±1°.

As used herein, the terms "containing" or "including (comprising)" may be open, semi-closed and closed. In other words, the terms also include "essentially consisting of" or "consisting of".

Compound of the Present Invention

The term "compound of the present invention" or "the crystal form of the present invention" or "the crystal form A of the compound of the present invention", as used herein, can be used interchangeably to refer to a crystalline compound having the formula I and the X-ray diffraction characteristic peaks as described in the first aspect of the present invention. The compound of the present invention can be used as sweeteners.

Composition

The present invention also provides a composition comprising a crystal form A compound of the present invention, i.e., a sweetener composition.

In a preferred embodiment of the present invention, the composition comprises a variety of different products such as food compositions, beverage compositions, and pharmaceutical compositions.

In a preferred embodiment, the content (wt %) of the compound of the present invention is from 0.1 to 99%, preferably from 1 to 90%, more preferably, from 2 to 50%, based on the total weight of the sweetener composition or product.

Other sweeteners such as lactose, fructose, sucrose, glucose, trehalose or combinations thereof may also be included in the sweetener composition of the present invention.

In a preferred embodiment, the sweetener composition contains no sucrose or a small amount of sucrose, and in the sweetener composition, the sucrose content (wt %)≤5, preferably ≤2, more preferably ≤1.

The present invention is further illustrated below in conjunction with specific embodiments. It is to be understood that the examples are not intended to limit the scope of the present invention. The experimental methods in the following examples which do not specify the specific conditions are usually in accordance with conventional conditions or according to the conditions recommended by the manufacturer. Percentages and parts are by weight unless otherwise stated.

Example 1

20 g of stevioside M having a matter purity of 99.5% was added to 100 mL of acetone at room temperature, stirred for 12 h, and filtered to obtain a white solid. The white solid was dried under vacuum at 25° C. to give a crystal form A of stevioside M.

Example 2

20 g of stevioside M having a matter purity of 99.5% was added to 100 mL of acetonitrile at room temperature, stirred for 24 h, and filtered to obtain a white solid. The white solid was dried under vacuum at 25° C. to give a crystal form A of stevioside M.

Example 3

20 g of stevioside M having a matter purity of 99.5% was added to 100 mL of ethanol at 50° C., stirred for 1 h, and filtered to obtain a white solid. The white solid was dried under vacuum at 25° C. to give a crystal form A of stevioside M.

Example 4

10 g of stevioside M having a matter purity of 50.2% was added to 1.5 L of methanol at 50° C., and stirred for 1 h. The filtrate after filtration was volatilized at 25° C. under vacuum pressure less than 0.5 MPa until the solvent volume was less than 50 mL, it was filtered, and the white solid was dried under vacuum at 25° C. to obtain a crystal form A of stevioside M.

Example 5

10 g of stevioside M having a matter purity of 50.2% was added to 1 L of ethanol at 50° C., stirred for 1 h, and the filtrate after filtration was volatilized at 50° C. until the solvent volume was less than 50 mL, it was filtered, and the white solid was blast dried at 50° C. to obtain a crystal form A of stevioside M.

Example 6

10 g of stevioside M having a matter purity of 40% was added to 900 mL of ethanol-water (2:1, v/v) solution at 50° C., stirred for 0.5 h, and the filtrate after filtration was volatilized at 50° C. under vacuum pressure less than 0.5 MPa until the solvent volume was less than 50 mL, it was filtered, and the white solid was dried under vacuum at 25° C. to obtain a crystal form A of stevioside M.

Example 7

10 g of stevioside M having a matter purity of 60% was added to 500 mL of ethanol-water (1:1, v/v) solution at 80° C., stirred for 0.5 h, and the filtered filtrate while hot was naturally cooled. After standing for 12 h, a large amount of solids were precipitated, and then filtered, and the white solid was dried under vacuum at 25° C. to obtain a crystal form A of stevioside M.

Example 8

10 g of stevioside M having a matter purity of 80% was added to 1 L of ethanol-water (1:1, v/v) solution at 50° C., stirred for 0.5 h, and the filtered filtrate while hot was reduced to 30° C. at a cooling rate of 1° C./h, and after the solid was precipitated, then filtered, and the white solid was dried under vacuum at 25° C. to obtain a crystal form A of stevioside M.

Example 9

10 g of stevioside M having a matter purity of 60% was added to 500 mL of ethanol-water (1:1, v/v) solution at 80° C., stirred for 0.5 h, and 0.1 g of stevioside M having a matter purity of 95% was added to the filtered filtrate while hot, followed by naturally cooling to room temperature, and the solid was precipitated after standing for 12 hours, and then filtered, and the white solid was dried under vacuum at 25° C. to obtain a crystal form A of stevioside M.

Example 10

20 g of crystal form A of stevioside M having a matter purity of 99.5% was added to 100 mL of water at room temperature, and stirred for 12 h, filtered to obtain a white solid, which is a crystal form B of stevioside M.

X-ray powder diffraction analysis (XRPD), differential scanning calorimetry analysis (DSC), thermogravimetric analysis (TG), dynamic moisture adsorption analysis (DVS) and the like were made for the crystal form A of stevioside M prepared in the above examples. XRPD analysis: It was tested at room temperature using a Bruker D8 advance type diffractometer from Bruker Instruments, Germany, Cu-Kα ray (λ=1.5418 Å) was used, the 2θ angle was scanned from 3 to 40 degrees, and the scanning speed was 0.2 degrees/second. The analysis results are shown in FIG. 1. The XRPD pattern shows that the crystal form A of stevioside M obtained in the above examples has good crystallinity.

In the sample powder X-ray powder diffraction pattern, the diffraction pattern obtained from a particular crystal form is often characteristic. Due to differences in crystallization conditions, particle size, relative content of the mixture, and other test conditions, the diffraction pattern may produce a preferred orientation effect, resulting in a change in the relative intensity of certain bands (especially at low angles) in the spectrum. Therefore, the relative intensities of the diffraction peaks are not characteristic for the crystals that are targeted, and it is more important to note the position of the peaks rather than their relative intensities when determining whether they are the same as the known crystal forms. In addition, it should be noted that the overall concept should be maintained when determining whether the crystal forms are the same, because it is not that a diffraction line represents a phase, but a specific set of "d-I/I1" data represents a phase. It should also be noted that in the identification of the mixture, some of the diffraction lines are missing due to factors such as a decrease in content. At this time, it is not necessary to rely on all the bands observed in the high-purity sample, and even a band may be characteristic for a given crystal.

Figure 2:
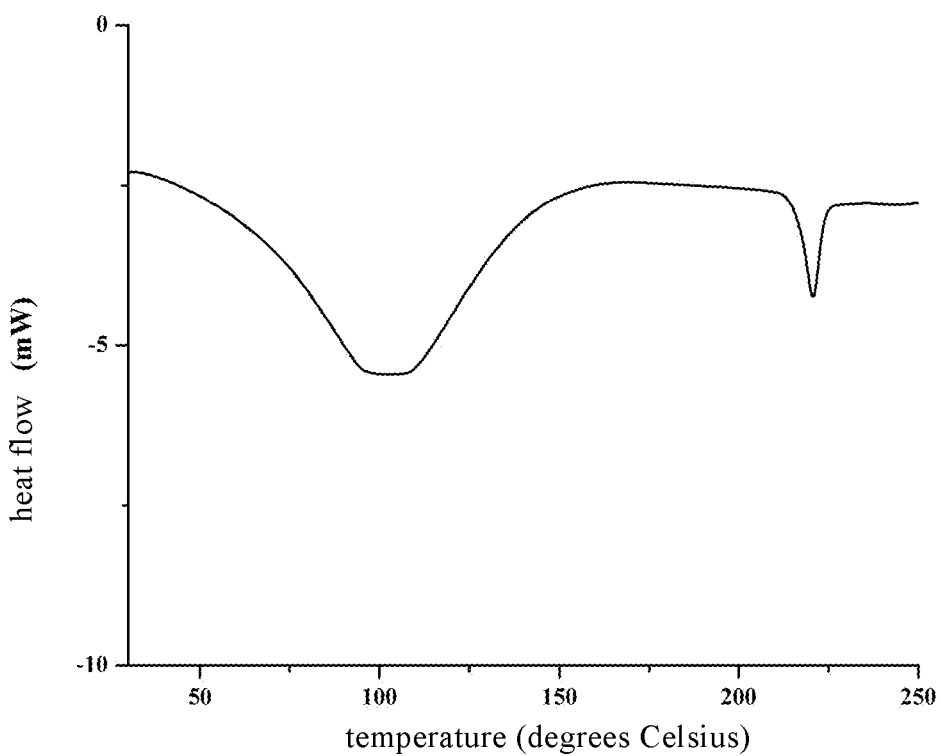
FIG. 2 is a differential scanning calorimetry (DSC) pattern of the crystal form A of stevioside M provided by the present invention.

DSC analysis: It was tested using a DSC 8500 type differential scanning calorimeter from Platinum Elmer, USA, with a nitrogen atmosphere at a heating rate of 10 degrees Celsius/minute. The analysis results are shown in FIG. 2.

Figure 3:
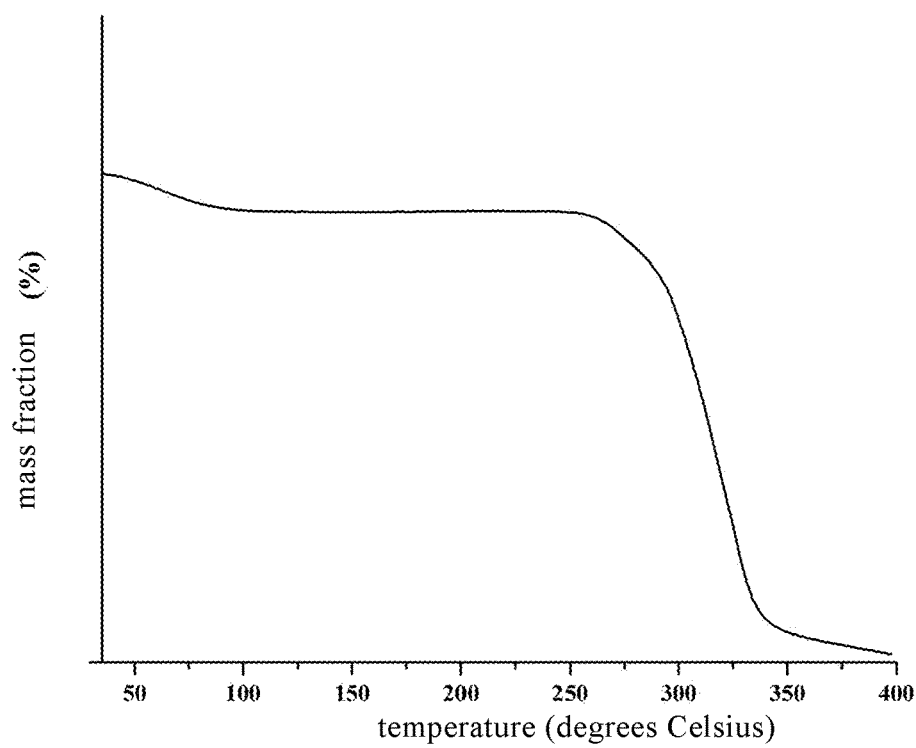
FIG. 3 is a thermogravimetric analysis (TG) pattern of the crystal form A of stevioside M provided by the present invention.

TG analysis: It was tested using the Netzsch TG 209F3 type thermogravimetric analyzer from NETZSCH, Germany. The temperature range was 30-400° C., the scanning rate was 10 K/min, and the purge gas was 25 mL/min. The analysis results are shown in FIG. 3.

Figure 4:
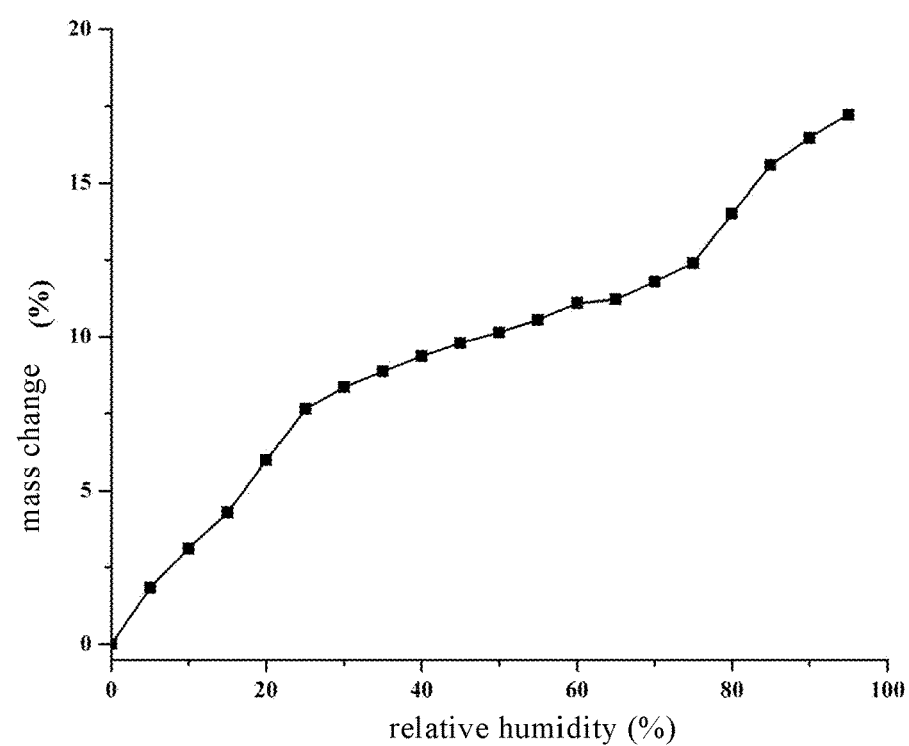
FIG. 4 is a dynamic vapor sorption (DVS) pattern of the crystal form A of stevioside M provided by the present invention.
Figure 6:
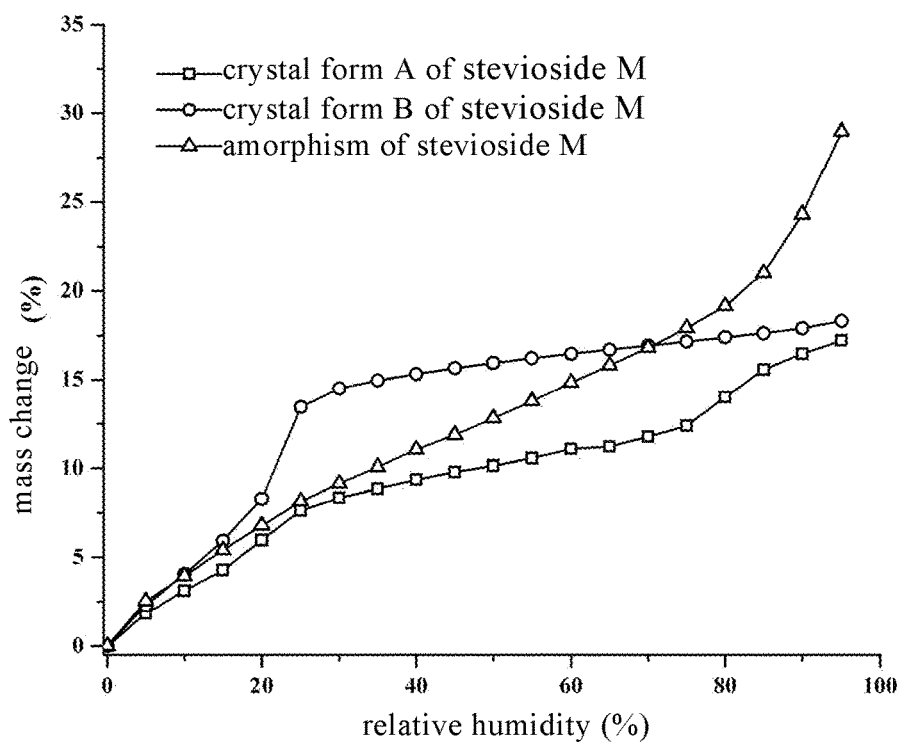
FIG. 6 is a comparison diagram of hygroscopicity (DVS) for the crystal form A, the crystal form B and the amorphism of stevioside M provided by the present invention.

DVS analysis: It was measured using DVS Intrinsic type dynamic moisture adsorption instrument from British SMS instrument company, measuring temperature: 25° C.; relative humidity: 0-95%. The analysis results are shown in FIG. 4. The crystal form A of stevioside M prepared in the above examples is significantly less hygroscopic than the amorphous form and the crystal form B of stevioside M at 25° C. and 40% RH. The comparison results are shown in FIG. 6 and Table 1. At the same time, the crystal form A of stevioside M is less hygroscopic than amorphism under normal storage (40%-80% RH).

TABLE 1

| sample name | hygroscopicity | hygroscopic mass change (0%-40% RH) | hygroscopic mass change (40%-80% RH) |
|---|---|---|---|
| crystal form A of stevioside M | 40% RH, 9.4% of water absorption; 80% RH, 14.0% of water absorption | 9.4% | 4.6% |
| crystal form B of stevioside M | 40% RH, 15.3% of water absorption 80% RH, 17.4% of water absorption | 15.3% | 2.1% |
| amorphism of stevioside M | 40% RH, 11.0% of water absorption 80% RH, 19.2% of water absorption | 11.0% | 8.2% |

Figure 7:
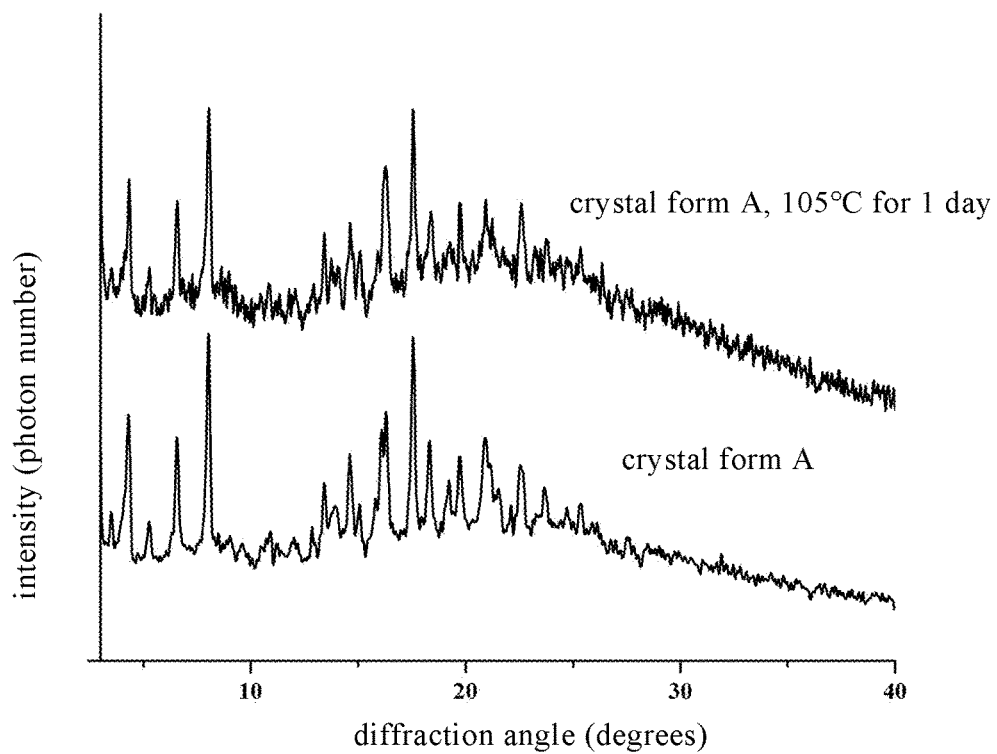
FIG. 7 is a comparison diagram of X-ray powder diffraction (XRPD) of the crystal form A of stevioside M provided by the present invention before and after drying.
Figure 8:
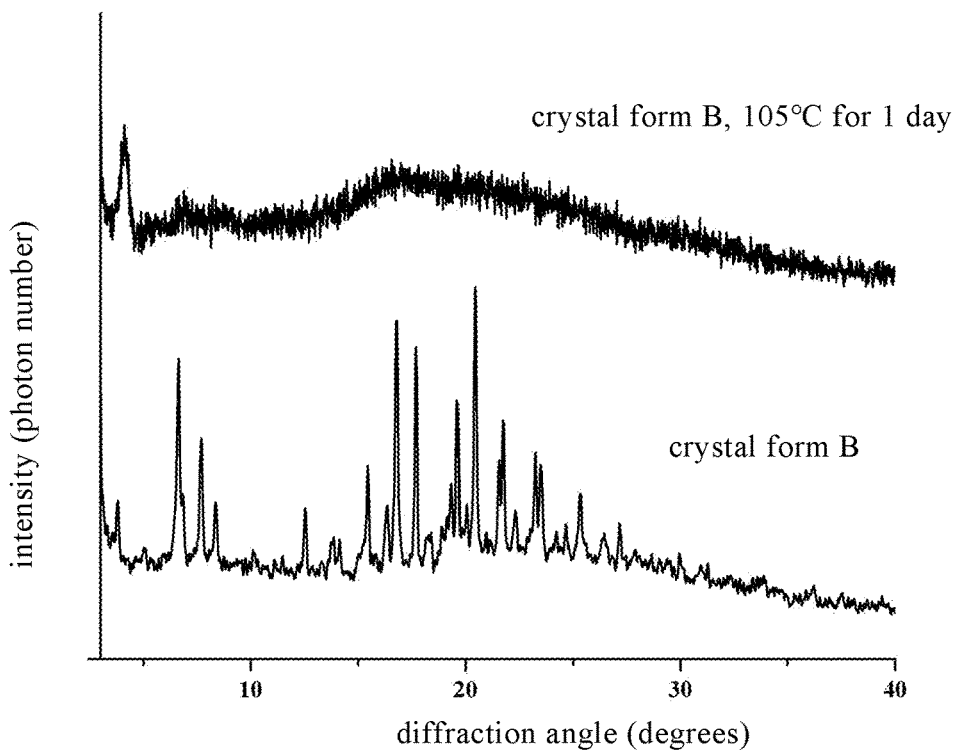
FIG. 8 is a comparison diagram of X-ray powder diffraction (XRPD) of the crystal form B of stevioside M provided by the present invention before and after drying.

The crystal form A of stevioside M prepared in the above examples was subjected to XRPD analysis after drying at 105° C. for one day, and the analysis results are shown in FIG. 7. It can be seen from FIG. 7 that the crystal form is unchanged, and the crystal form has good stability under high temperature conditions. The crystal form B of stevioside M is extremely unstable under high temperature conditions, and which is amorphous after drying for one day at 105° C., and the analysis results are shown in FIG. 8.

Figure 9:
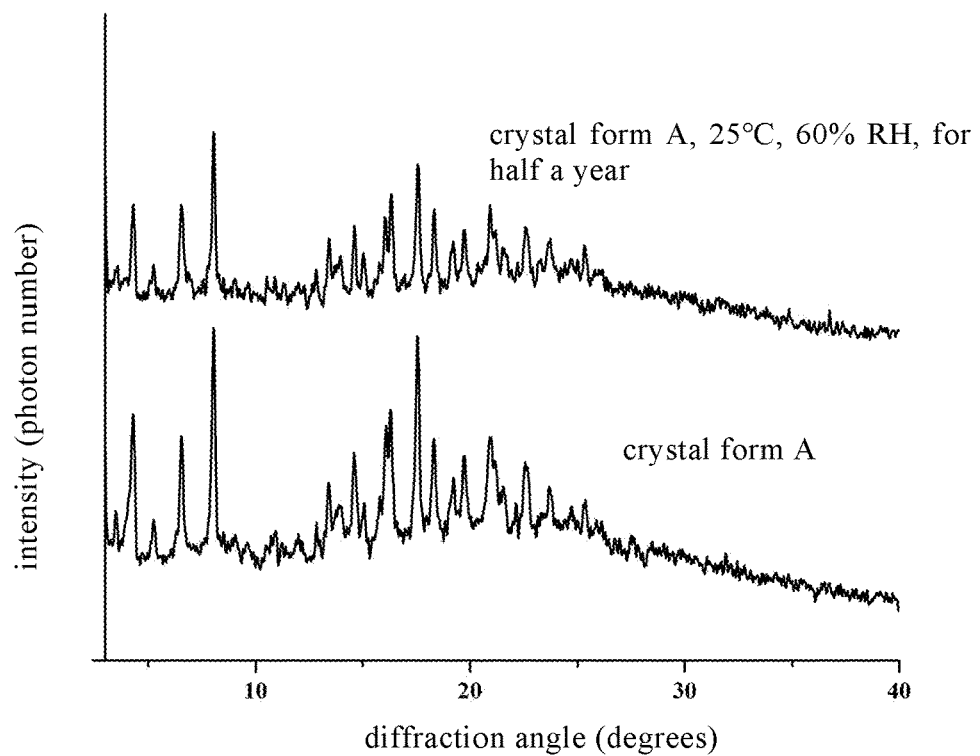
FIG. 9 is a comparison diagram of X-ray powder diffraction (XRPD) of the crystal form A of stevioside M provided by the present invention stored at 25° C. and a relative humidity of 60% for half a year.

The crystal form A of stevioside M prepared in the above examples was stored at 25° C. and RH 60% for half a year, and the analysis results are shown in FIG. 9. It can be seen from FIG. 9 that the crystal form is unchanged, indicating that the crystal form has good physical stability under normal storage conditions.

HPLC analysis: It was determined using a 1260 infinity liquid chromatograph from Agilent Technologies, Inc., USA. Sample solution preparation method: 25-50 mg of stevioside M sample was accurately weighed, and added into a 25 ml volumetric flask, then water-acetonitrile (7:3, v/v) solution was added, dissolved to volume. Preparation method of sodium phosphate buffer (specification: 10 mmol/L, pH: 2.6): dissolving 2.76 g of sodium dihydrogen phosphate into 2 liters of water, adding phosphoric acid, and the pH was adjusted to 2.6. Chromatographic column: Luna 5μ C18(2) 100 A column from Phenomenex. Injection volume: 5 μl. Flow rate: 1.0 mL/min. Column temperature: 40° C. Detector: UV detection at 210 nm. The elution gradient is shown as follows:

| time (minutes) | sodium phosphate buffer (specification: 10 mmol/L, pH: 2.6)% | acetonitrile % |
|---|---|---|
| 0.00 | 80 | 20 |
| 2.00 | 80 | 20 |
| 10.00 | 60 | 40 |
| 15.00 | 60 | 40 |
| 21.00 | 80 | 20 |
| 24.00 | 80 | 20 |

Figure 10:
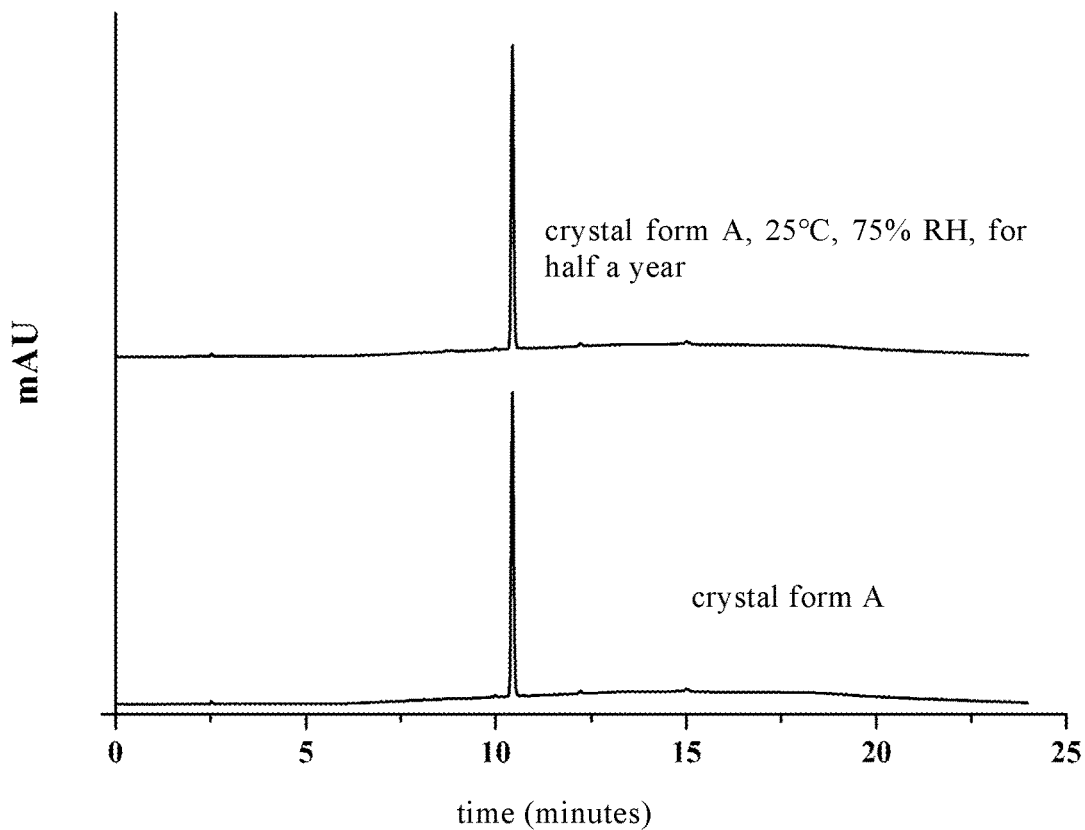
FIG. 10 is a high performance liquid chromatography (HPLC) comparison diagram of the crystal form A of stevioside M provided by the present invention stored at 40° C. and a relative humidity of 75% for half a year.

The analysis results are shown in FIG. 10. The crystal form A of stevioside M prepared in the above examples has good chemical stability, and the HPLC analysis shows that the content is reduced by less than 0.2% after storage for half a year at 40° C. and RH 75%, indicating that the crystal form has good chemical stability under high humidity conditions.

Figure 11:
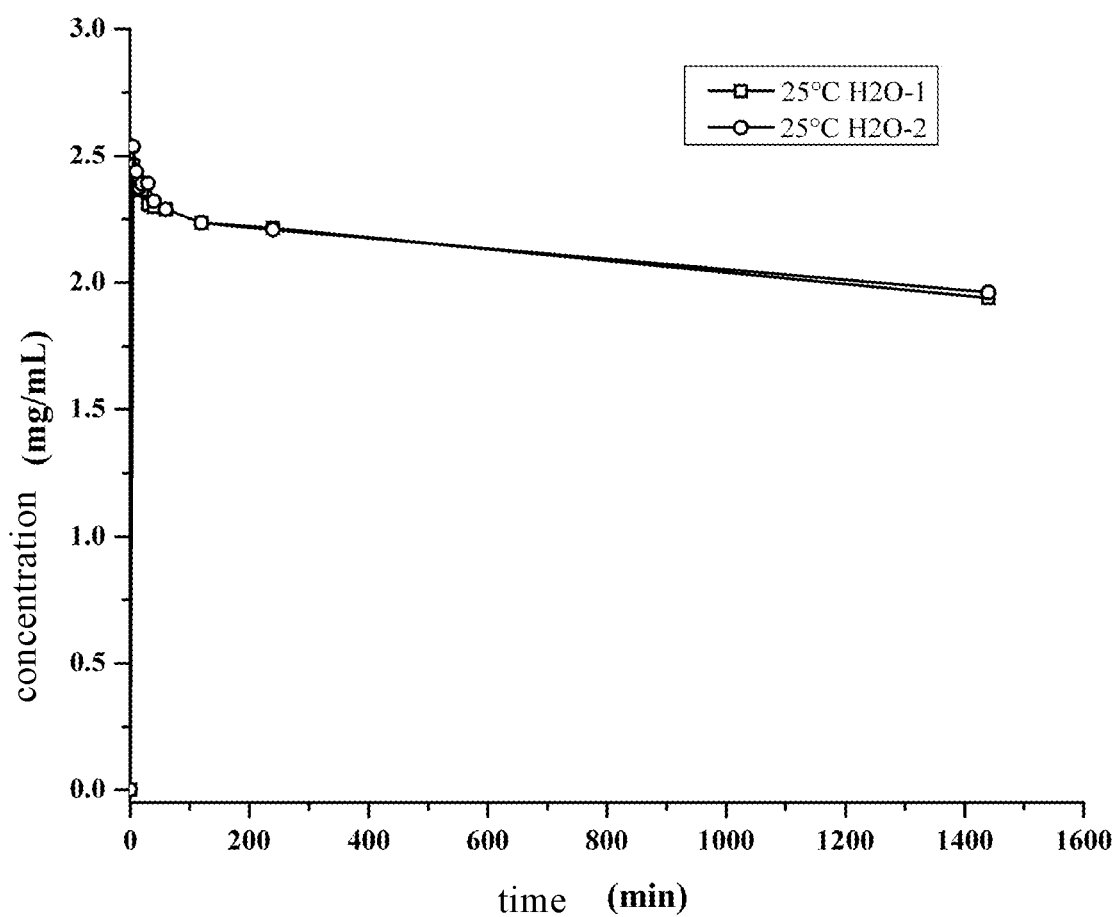
FIG. 11 is a powder dissolution profile of the crystal form A of stevioside M provided by the present invention.

The crystal form A of stevioside M prepared in the above examples has good reproducibility and is stable in water solubility, and has a maximum solubility of about 3 mg/mL, and the equilibrium solubility is about 2 mg/mL at 24 hours. The powder dissolution profiles of the two batches of crystal form A of stevioside M prepared by the examples are shown in FIG. 11. The water solubility of crystal form A is similar to that of the stevioside D-stevioside M amorphous composition (about 3 mg/mL) disclosed in Patent CN 105722533 A, and both of which can stably increase the water solubility by 2-3 times.

The stevioside M raw material used in the above examples was supplied by Shandong Zhucheng Haotian Pharmaceutical Co., Ltd.

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

The invention claimed is:

1. A crystal form A of stevioside M, wherein the structure is as shown in Formula I,

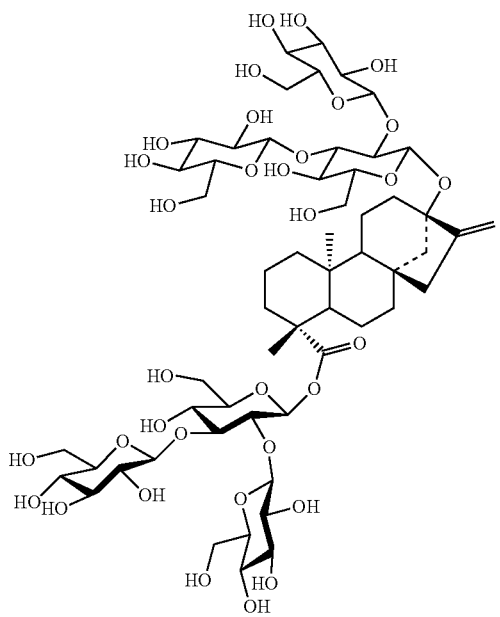

(I)

and, in an X-ray powder diffraction method using Cu-Kα, the crystal form A has 3, 4, 5 or 6 characteristic diffraction peaks at about 4.30, about 6.57, about 8.04, about 16.31, about 17.57 and about 20.91, with the 2θ angles expressed in degrees.

2. The crystal form A of stevioside M of claim 1, wherein the crystal form A has an X-ray powder diffraction (XRPD) pattern substantially as shown in FIG. 1, and a 2θ value expressed in degrees with an error range of ±1°, an interplanar spacing d expressed in Å and a relative intensity of the diffraction peaks expressed in percentage having the following characteristics:

| 2θ angle (±1°) | d(Å) | relative intensity % |
|---|---|---|
| 3.51 | 25.12 | 14.4 |
| 4.30 | 20.54 | 63.7 |

-continued

| 2θ angle (±1°) | d(Å) | relative intensity % |
|---|---|---|
| 5.27 | 16.75 | 17.7 |
| 6.57 | 13.44 | 54.4 |
| 8.04 | 10.99 | 100.0 |
| 13.43 | 6.59 | 28.8 |
| 14.61 | 6.06 | 39.9 |
| 16.31 | 5.43 | 59.5 |
| 17.57 | 5.04 | 87.7 |
| 18.34 | 4.83 | 40.8 |
| 19.25 | 4.61 | 22.5 |
| 19.75 | 4.49 | 32.1 |
| 20.91 | 4.24 | 42.6 |
| 22.56 | 3.94 | 31.5 |
| 23.67 | 3.76 | 19.5. |

Figure 5:
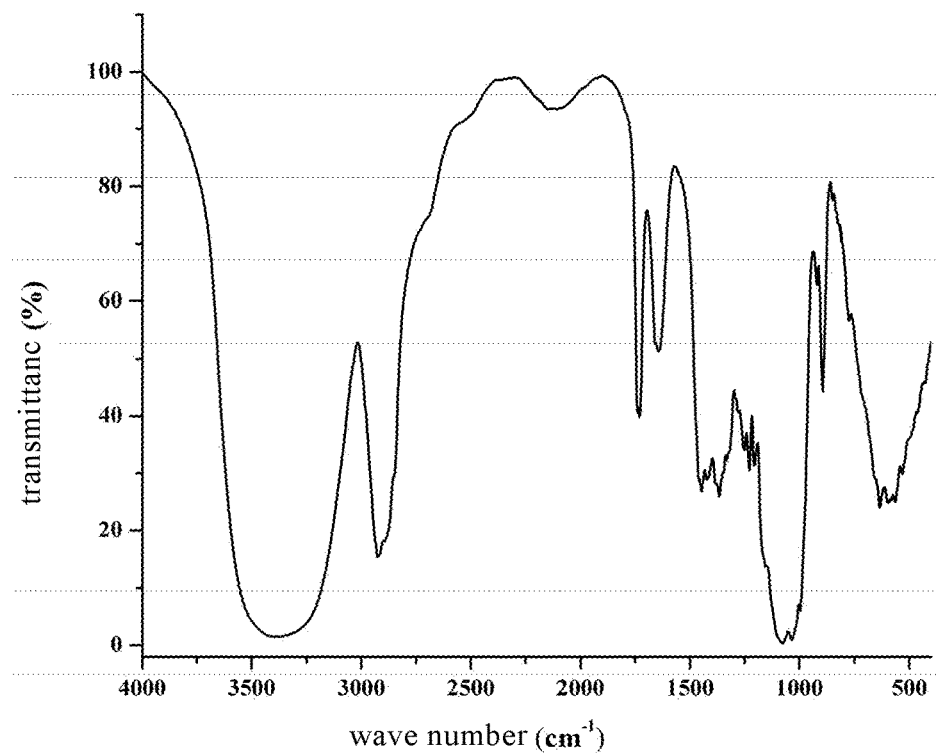
FIG. 5 is an infrared (IR) diagram of the crystal form A of stevioside M provided by the present invention.

3. The crystal form A of stevioside M of claim 1, wherein the crystal form A also has one or more characteristics selected from the group consisting of:
   (1) the crystal form A has a differential scanning calorimetry pattern substantially as shown in FIG. 2;
   (2) the crystal form A has a thermogravimetric analysis pattern substantially as shown in FIG. 3;
   (3) the crystal form A has a dynamic moisture adsorption profile substantially as shown in FIG. 4; and
   (4) the crystal form A has an infrared spectrum substantially as shown in FIG. 5.

4. A method for producing the crystal form A of stevioside M of claim 1, which is a mixed crystallization method of one or two or more of a suspension method, a solution evaporation method or a cooling method, comprising the following steps:
   (1) suspending: mixing stevioside M with a solvent for 0.1-48 h in a temperature range of 0-100° C. to obtain a suspension solution;
   (2) cooling: filtering the suspension solution in step (1) while hot, and cooling the filtrate to a temperature range of 0-30° C. until a large amount of white solid is precipitated to obtain a suspension solution;
   (3) volatilization: under a vacuum pressure less than or equal to 0.1 MPa, volatilizing the suspension solution in step (1) in a temperature range of 0-100° C. after filtering until a large amount of white solid is precipitated to obtain a suspension solution; and
   (4) filtration: filtering or centrifuging the suspension solution in step (1), (2) or (3) in a temperature range of 0-100° C. to obtain a white solid, which is dried to obtain the crystal form A of stevioside M.

5. The method for producing the crystal form A of stevioside M of claim 4, wherein the dry matter purity of the stevioside M in step (1) is in a range of 20-100%.

6. The method for producing the crystal form A of stevioside M of claim 4, wherein the solvent in step (1) is: one or two or more of methanol, ethanol, 1-propanol, acetonitrile, acetone, methyl ethyl ketone, methyl acetate, ethyl formate, ethyl acetate, methyl ter-butyl ether, tetrahydrofuran, nitromethane and methylbenzene, or a mixed solvent of the above solvent and water.

7. A composition, comprising the crystal form A of stevioside M of claim 1.

* * * * *